(12) United States Patent
Chang et al.

(10) Patent No.: US 9,013,010 B2
(45) Date of Patent: Apr. 21, 2015

(54) NANOPORE SENSOR DEVICE

(71) Applicant: International Business Machines Corporation, Armonk, NY (US)

(72) Inventors: Josephine B. Chang, Mahopac, NY (US); Michael A. Guillorn, Yorktown Heights, NY (US); Eric A. Joseph, White Plains, NY (US); Satyavolu S. Papa Rao, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 15 days.

(21) Appl. No.: 14/013,598

(22) Filed: Aug. 29, 2013

(65) Prior Publication Data

US 2014/0183668 A1  Jul. 3, 2014

Related U.S. Application Data

(63) Continuation of application No. 13/733,404, filed on Jan. 3, 2013.

(51) Int. Cl.
*H01L 27/14* (2006.01)
*H01L 29/66* (2006.01)
*G01N 33/543* (2006.01)
(Continued)

(52) U.S. Cl.
CPC .... *H01L 29/66007* (2013.01); *G01N 33/54373* (2013.01); *B01L 3/502707* (2013.01); *G01N 33/48721* (2013.01); *H01L 29/66* (2013.01)

(58) Field of Classification Search
USPC ........................................................ 257/414
See application file for complete search history.

(56) References Cited

U.S. PATENT DOCUMENTS 6,914,256 B2   7/2005   Zhang et al.
7,235,475 B2   6/2007   Kamins
(Continued)

FOREIGN PATENT DOCUMENTS

KR   1020060048187   5/2006
WO   2005119253 A1   12/2005

OTHER PUBLICATIONS

Office Action, dated Oct. 23, 2013, received in a related U.S. Appl. No. 13/733,404.
(Continued)

*Primary Examiner* — Matthew Landau
*Assistant Examiner* — Igwe U Anya
(74) *Attorney, Agent, or Firm* — Scully, Scott, Murphy & Presser, P.C.; Louis J. Percello, Esq.

(57) ABSTRACT

A pair of electrode plates can be provided by directional deposition and patterning of a conductive material on sidewalls of a template structure on a first dielectric layer. An electrode line straddling the center portion is formed. A dielectric spacer and a conformal conductive layer are subsequently formed. Peripheral electrodes laterally spaced from the electrode line are formed by pattering the conformal conductive layer. After deposition of a second dielectric material layer that encapsulates the template structure, the template structure is removed to provide a cavity that passes through the pair of electrode plates, the electrode line, and the peripheral electrodes. A nanoscale sensor thus formed can electrically characterize a nanoscale string by passing the nanoscale string through the cavity while electrical measurements are performed employing the various electrodes.

20 Claims, 26 Drawing Sheets

(51) Int. Cl.
  *G01N 33/487* (2006.01)
  *B01L 3/00* (2006.01)

(56) References Cited

U.S. PATENT DOCUMENTS

| | | | |
|---|---|---|---|
| 8,129,978 B2 | 3/2012 | Nakazato | |
| 8,138,491 B2 | 3/2012 | Appenzeller et al. | |
| 8,236,595 B2* | 8/2012 | Agarwal et al. | 438/49 |
| 2003/0215974 A1 | 11/2003 | Kawasaki et al. | |
| 2004/0181630 A1* | 9/2004 | Jaiprakash et al. | 711/127 |
| 2005/0053525 A1* | 3/2005 | Segal et al. | 422/88 |
| 2005/0065741 A1* | 3/2005 | Segal et al. | 702/57 |
| 2006/0138575 A1 | 6/2006 | Kamins | |
| 2006/0170012 A1 | 8/2006 | Larmer et al. | |
| 2007/0170540 A1 | 7/2007 | Chung et al. | |
| 2008/0274576 A1 | 11/2008 | Enomoto et al. | |
| 2010/0066348 A1 | 3/2010 | Merz et al. | |
| 2010/0327380 A1 | 12/2010 | Chang | |
| 2011/0236984 A1 | 9/2011 | Sun et al. | |
| 2011/0272693 A1 | 11/2011 | Kobayashi et al. | |
| 2012/0007150 A1* | 1/2012 | Caligiore et al. | 257/254 |
| 2012/0011875 A1 | 1/2012 | Oh et al. | |
| 2012/0061239 A1* | 3/2012 | Elibol et al. | 204/406 |
| 2012/0118739 A1 | 5/2012 | Walavalkar et al. | |
| 2013/0009214 A1* | 1/2013 | Bustillo et al. | 257/253 |
| 2013/0126994 A1 | 5/2013 | Hwang et al. | |
| 2013/0334579 A1* | 12/2013 | Accardi et al. | 257/253 |

OTHER PUBLICATIONS

Office Action, dated Apr. 30, 2014, received in a related U.S. Patent Application, namely U.S. Appl. No. 13/733,404.

Bhattacharya, S. et al., "An Accurate DNA Sensing and Diagnosis Methodology Using Fabricated Silicon Nanopores" IEEE Transactions on Circuits and Systems-I: Regular Papers (Nov. 2006) pp. 2377-2383, vol. 53, No. 11.

\* cited by examiner

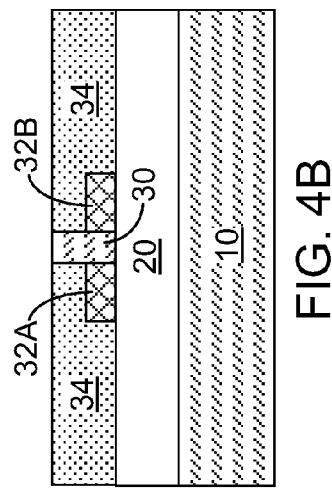
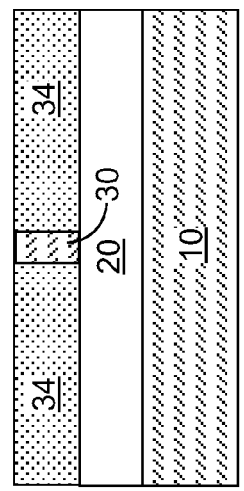
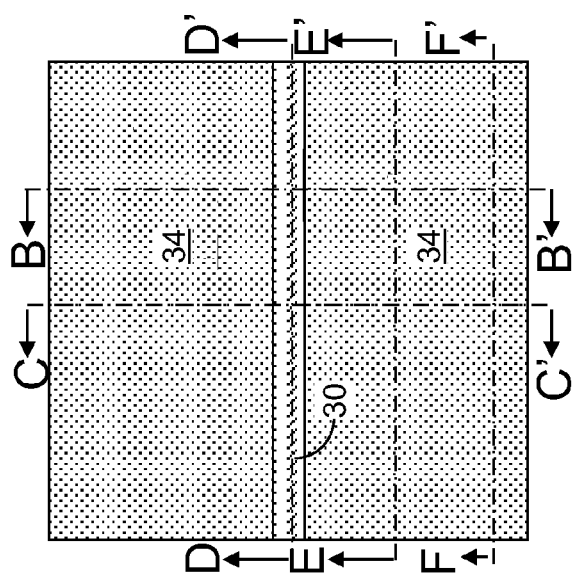

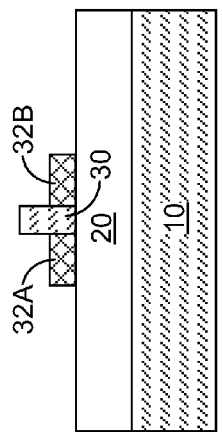
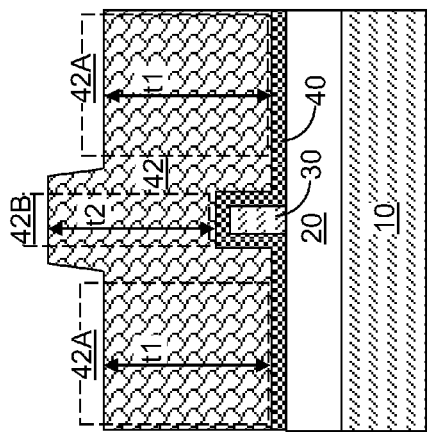
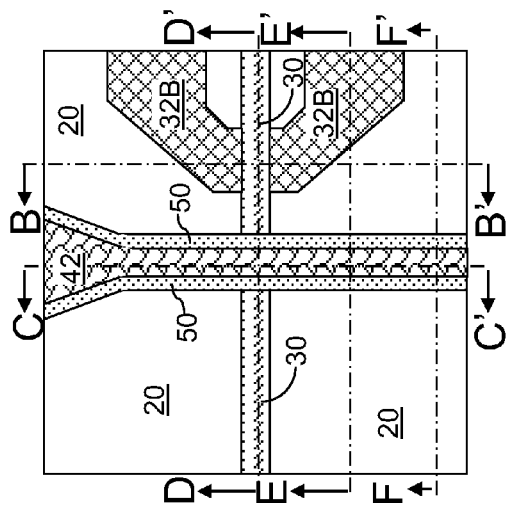

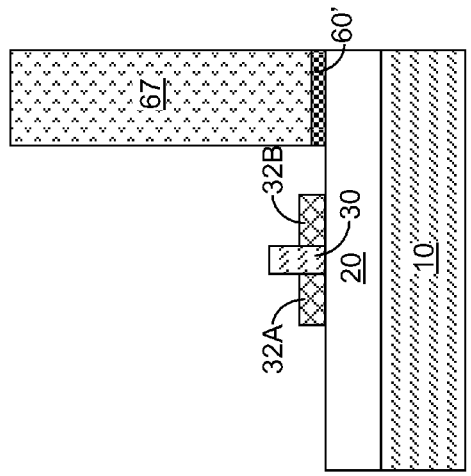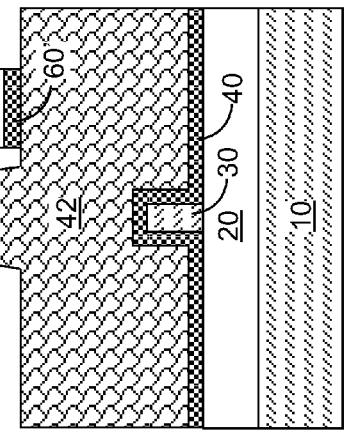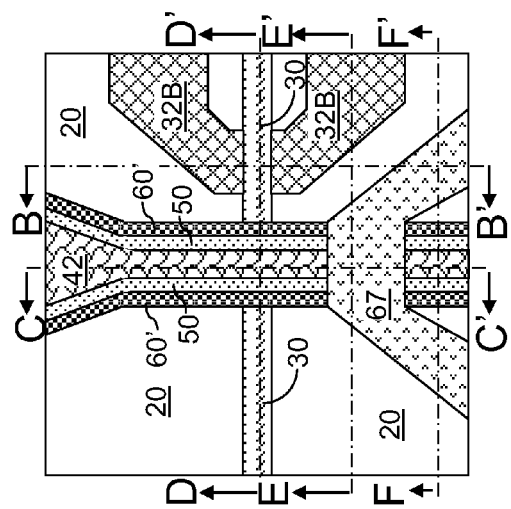

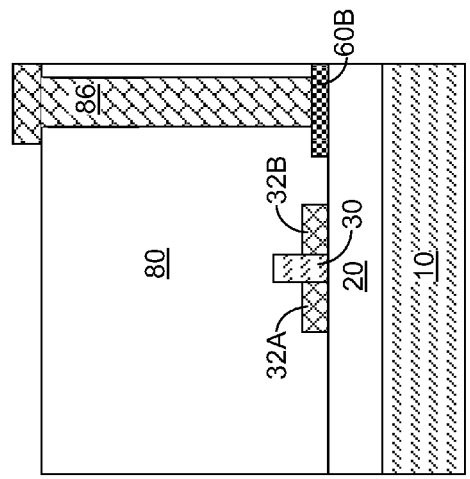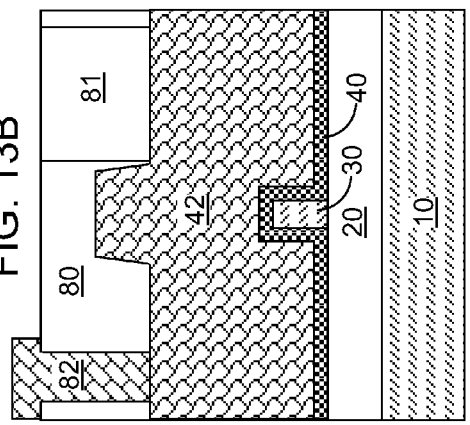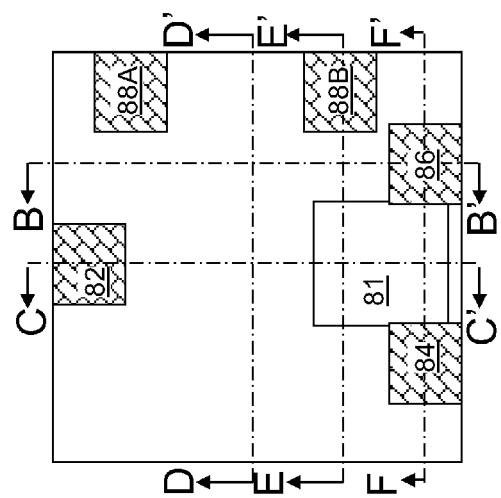

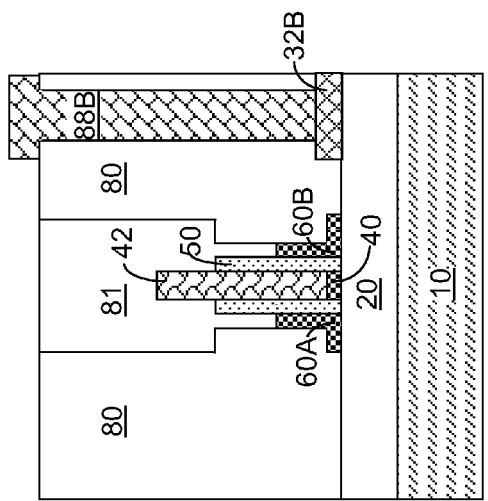
FIG. 13D
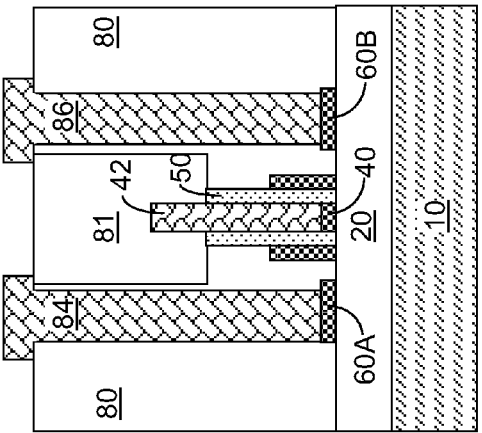
FIG. 13E
FIG. 13F

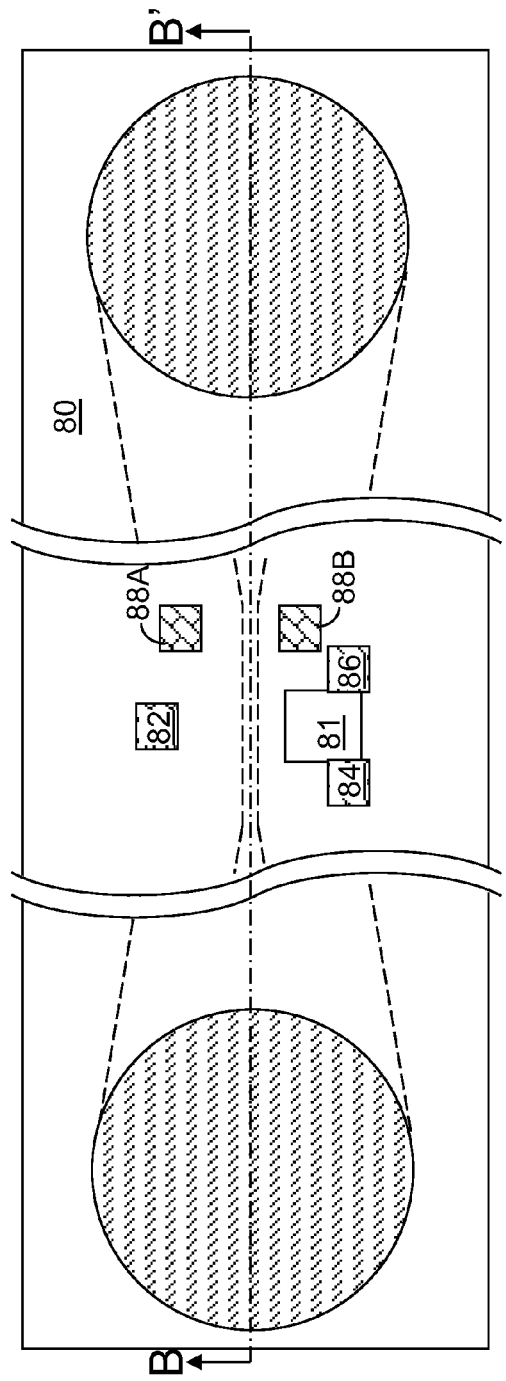
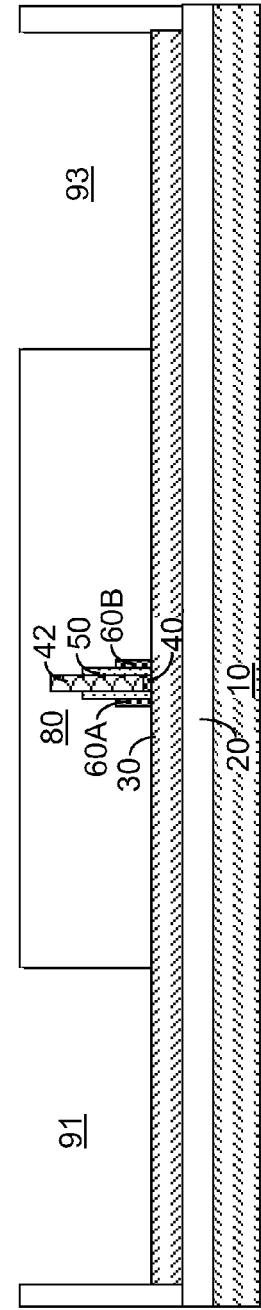
FIG. 14A
FIG. 14B

NANOPORE SENSOR DEVICE

CROSS REFERENCE TO RELATED APPLICATION

This application is a continuation of U.S. patent application Ser. No. 13/733,404 filed Jan. 3, 2013 the entire content and disclosure of which is incorporated herein by reference.

BACKGROUND

The present disclosure relates to a nanopore sensor device, and more particularly to a nanopore sensor device configured to determine electrical properties of a nanoscale string such as deoxyribonucleic acid (DNA) along a lengthwise direction, and a method of manufacturing the same.

Determination of electrical properties of a nanoscale string is useful in determining molecular structures of the nanoscale string. For example, determination of electrical properties of a DNA string can provide information on the sequence of the molecules within the DNA string, and enable decoding of the DNA sequence within the DNA string. A device is desired that can provide direct reading of electrical properties of the molecules within a nanoscale string along the lengthwise direction.

SUMMARY

A nanoscale sensor device can be fabricated by providing a template structure on a first dielectric material layer. The template structure includes a center portion and two funnel shaped portions attached to the center portion and having a gradually increasing width with distance from the center portion. A pair of electrode plates for applying an electrical field perpendicular to a lengthwise direction of a nanoscale string can be provided by directional deposition and patterning of a conductive material on sidewalls of the template structure. A cluster of electrode pairs can be provided by forming an electrode line straddling the center portion, forming a dielectric spacer around the electrode line, forming a conformal conductive layer, and patterning the conductive layer. Remaining portions of the conformal conductive layer constitute peripheral electrodes laterally spaced from the electrode line by a same distance along the lengthwise direction of the template structure. After deposition of a second dielectric material layer that encapsulates the template structure, the template structure is removed to provide a cavity that passes through the pair of electrode plates, the electrode line, and the peripheral electrodes. A nanoscale string can be electrically characterized while passing through the cavity employing the various electrodes.

According to an aspect of the present disclosure, a method of forming a sensor structure is provided. A template structure is formed on a first dielectric material layer. An electrode line straddling the template structure is formed. A second dielectric material layer is formed over the template structure. The template structure is removed selective to the first and second dielectric material layers to form a cavity. A sensor structure including the cavity and at least the electrode line is thus formed.

According to another aspect of the present disclosure, a sensor structure includes a first dielectric material layer and a second dielectric material layer in contact with each other at a planar interface. A cavity is embedded within the first dielectric material layer and the second dielectric material layer. The sensor structure further includes an electrode line embedded within the second dielectric material layer and straddling the cavity. First portions of the electrode line are in contact with a surface of the first dielectric material layer, and a second portion of the electrode line that is not in contact with the first dielectric material layer is spaced from a plane including the interface by a uniform distance.

BRIEF DESCRIPTION OF SEVERAL VIEWS OF THE DRAWINGS

FIG. 4A is a top-down view of the selected portion of the exemplary structure after deposition and planarization of a dielectric masking material layer and removal of a conductive material portion according to an embodiment of the present disclosure.

FIG. 4B is a vertical cross-sectional view of the selected portion of the exemplary structure along the vertical plane B-B' of FIG. 4A.

FIG. 4C is a vertical cross-sectional view of the selected portion of the exemplary structure along the vertical plane C-C' of FIG. 4A.

FIG. 7A is a top-down view of the selected portion of the exemplary structure after formation of a dielectric spacer around the electrode line according to an embodiment of the present disclosure.

FIG. 7B is a vertical cross-sectional view of the selected portion of the exemplary structure along the vertical plane B-B' of FIG. 7A.

FIG. 7C is a vertical cross-sectional view of the selected portion of the exemplary structure along the vertical plane C-C' of FIG. 7A.

FIG. 9A is a top-down view of the selected portion of the exemplary structure after application and patterning of a photoresist layer and an anisotropic etch according to an embodiment of the present disclosure.

FIG. 9B is a vertical cross-sectional view of the selected portion of the exemplary structure along the vertical plane B-B' of FIG. 9A.

FIG. 9C is a vertical cross-sectional view of the selected portion of the exemplary structure along the vertical plane C-C' of FIG. 9A.

FIG. 13A is a top-down view of the selected portion of the exemplary structure after formation of contact via structures through the second dielectric material layer according to an embodiment of the present disclosure.

FIG. 13B is a vertical cross-sectional view of the selected portion of the exemplary structure along the vertical plane B-B' of FIG. 13A.

FIG. 13C is a vertical cross-sectional view of the selected portion of the exemplary structure along the vertical plane C-C' of FIG. 13A.

FIG. 13D is a vertical cross-sectional view of the selected portion of the exemplary structure along the vertical plane D-D' of FIG. 13A.

FIG. 13E is a vertical cross-sectional view of the selected portion of the exemplary structure along the vertical plane E-E' of FIG. 13A.

FIG. 13F is a vertical cross-sectional view of the selected portion of the exemplary structure along the vertical plane F-F' of FIG. 13A.

FIG. 14A is a top-down view of the exemplary structure after formation of via cavities through the second dielectric material layer according to an embodiment of the present disclosure.

FIG. 14B is a vertical cross-sectional view of the exemplary structure along the vertical plane B-B' of FIG. 14A.

DETAILED DESCRIPTION

Figure 1A:
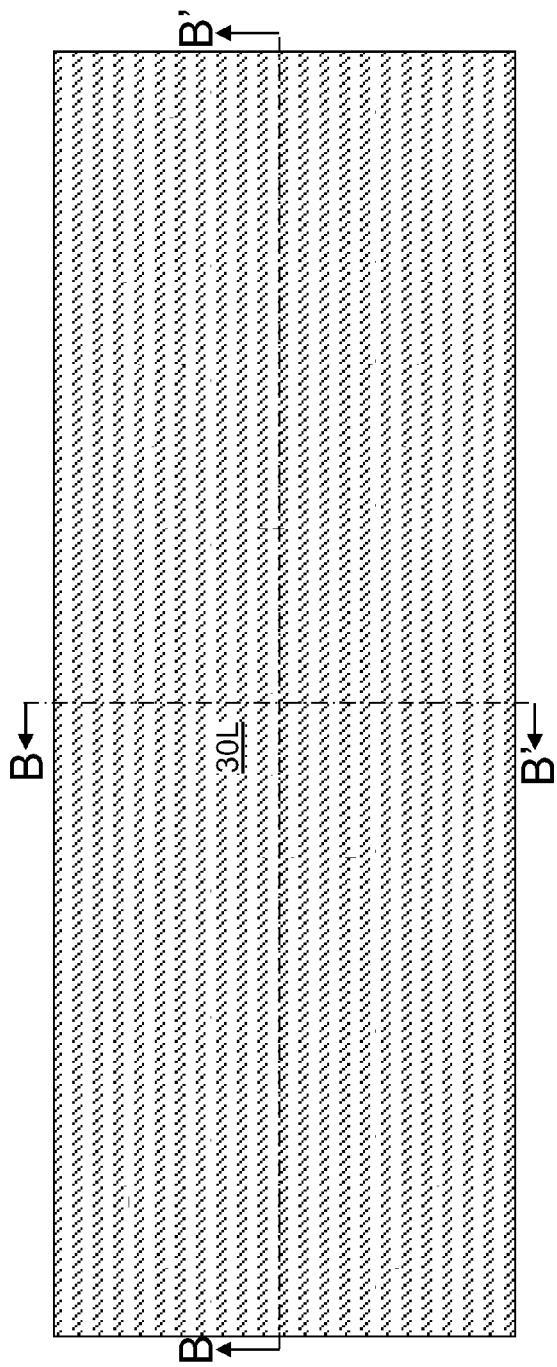
FIG. 1A is a top-down view of an exemplary structure including a substrate, a first dielectric material layer, and a sacrificial material layer according to an embodiment of the present disclosure.

As stated above, the present disclosure relates to a nanopore sensor device configured to determine electrical properties of a nanoscale string such as deoxyribonucleic acid (DNA) along a lengthwise direction, and a method of manufacturing the same. Aspects of the present disclosure are now described in detail with accompanying figures. It is noted that like reference numerals refer to like elements across different embodiments. The drawings are not necessarily drawn to scale.

Figure 1B:
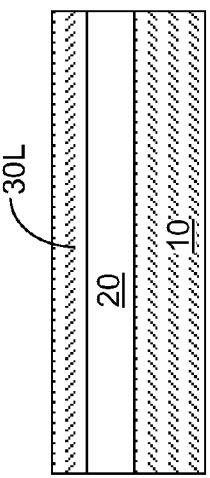
FIG. 1B is a vertical cross-sectional view of the exemplary structure along the vertical plane B-B' of FIG. 1A.

Referring to FIGS. 1A and 1B, an exemplary structure according to an embodiment of the present disclosure includes starting substrate which is a vertical stack of a handle substrate 10, a first dielectric material layer 20, and a top sacrificial layer 30L. The handle substrate 10 can include a semiconductor material, a dielectric material, a conductive material, or a stack thereof. The handle substrate 10 can have a thickness from 50 microns to 2 mm, and provides mechanical support to the first dielectric material layer 20.

The first dielectric material layer 20 includes a dielectric material such as silicon oxide, silicon nitride, silicon oxynitride, a dielectric metal oxide, a dielectric metal nitride, a dielectric metal oxynitride, or a combination thereof. The first dielectric material layer 20 is a buried insulator layer located between the handle substrate 10 and the top sacrificial layer 30. The thickness of the first dielectric material layer 20 can be from 5 nm to 50 microns, although lesser and greater thicknesses can also be employed.

The top semiconductor layer 30L includes a sacrificial material, which can be a single crystalline, polycrystalline, or amorphous semiconductor material. The sacrificial material of the layer 30L can be, for example, the top single crystalline Si layer of an SOI (Silicon on Insulator) substrate, or a poly-Si or poly-Ge layer deposited using chemical vapor deposition. The thickness of the top semiconductor layer 30L can be from 5 nm to 1,000 nm, although lesser and greater thicknesses can also be employed.

Figure 2A:
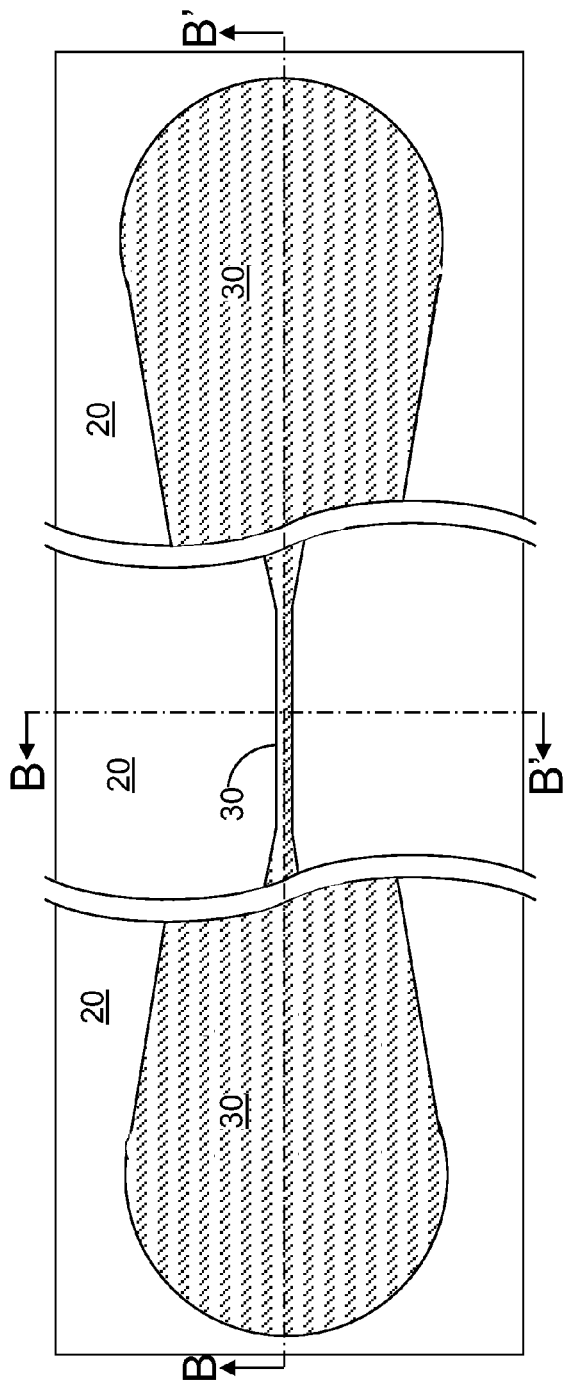
FIG. 2A is a top-down view of the exemplary structure after patterning the sacrificial material into a template structure according to an embodiment of the present disclosure.
Figure 2B:
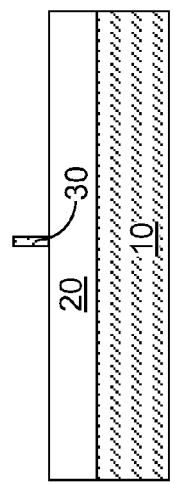
FIG. 2B is a vertical cross-sectional view of the exemplary structure along the vertical plane B-B' of FIG. 2A.
Figure 3A:
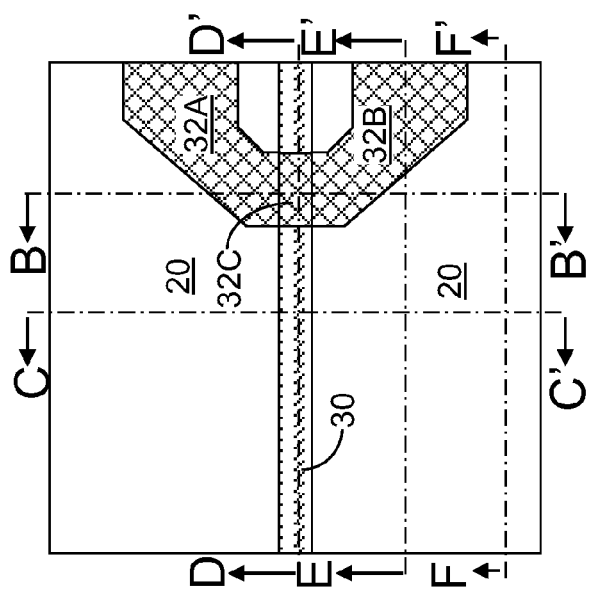
FIG. 3A is a top-down view of a selected portion of the exemplary structure after formation of a pair of electrode plates on sidewalls of the sacrificial template structure according to an embodiment of the present disclosure.
Figure 3B:
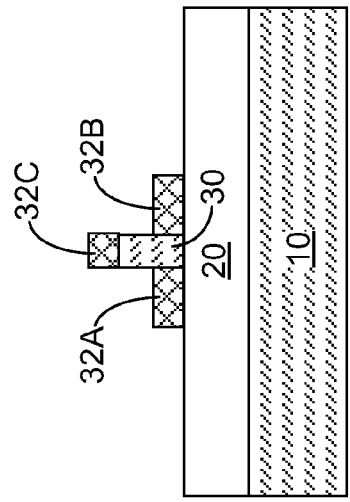
FIG. 3B is a vertical cross-sectional view of the selected portion of the exemplary structure along the vertical plane B-B' of FIG. 3A.
Figure 3C:
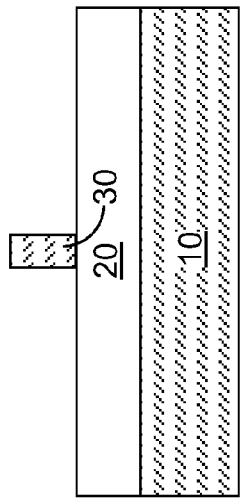
FIG. 3C is a vertical cross-sectional view of the selected portion of the exemplary structure along the vertical plane C-C' of FIG. 3A.
Figure 3D:
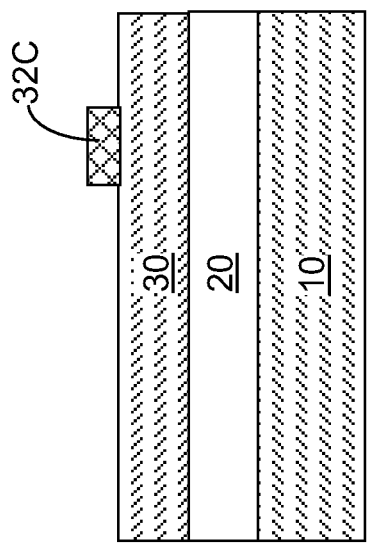
FIG. 3D is a vertical cross-sectional view of the selected portion of the exemplary structure along the vertical plane D-D' of FIG. 3A.
Figure 3E:
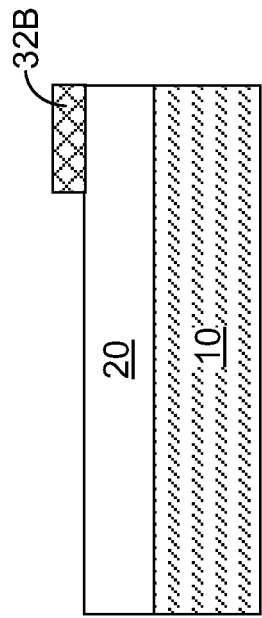
FIG. 3E is a vertical cross-sectional view of the selected portion of the exemplary structure along the vertical plane E-E' of FIG. 3A.
Figure 3F:
FIG. 3F is a vertical cross-sectional view of the selected portion of the exemplary structure along the vertical plane F-F' of FIG. 3A.

Referring to FIGS. 2A and 2B, a template structure 30 is formed on the first dielectric material layer 20 by patterning the top sacrificial layer 30L. For example, a photoresist layer (not shown) is applied over the top sacrificial layer 30L and lithographically patterned. The patterned photoresist layer covers a contiguous region including a uniform width region having a uniform width, a first tapered region adjoined to the uniform width region and having a first variable width that increases with distance from the uniform width region, and a second tapered region adjoined to the uniform width region and having a second variable width that increases with distance from the uniform width region. As used herein, a "uniform" width refers to a width that is invariant under translation along a lateral direction perpendicular to the direction of the width.

The pattern in the patterned photoresist layer is transferred into the top semiconductor layer 30L by an etch, which can be, for example, an anisotropic etch such as a reactive ion etch. The template structure 30 can be a remaining portion of the top semiconductor layer 30L after the etch. Optionally, a lateral etch may be employed to reduce lateral dimensions of the template structure 30. The template structure 30 includes a uniform width semiconductor region having a uniform width throughout, a first tapered semiconductor region adjoined to the uniform width semiconductor region at a proximal end thereof and having a first variable width that increases with distance from the uniform width semiconductor region, and a second tapered semiconductor region adjoined to the uniform width semiconductor region at a proximal end thereof and having a second variable width that increases with distance from the uniform width semiconductor region. In one embodiment, the sidewalls of the template structure 30 can be vertical.

The uniform width semiconductor region of the template structure can have a width in a range from 1 nm to 1,000 nm, although lesser and greater widths can also be employed. The taper angles of the first tapered semiconductor region and the second tapered semiconductor region may be the same or different, and can be in a range from 0.01 degree to 45 degrees, although lesser and greater angles can also be employed. Each taper angle is measured between a sidewall surface of the first or second tapered semiconductor region and the lengthwise direction of the uniform width semiconductor region, i.e., the horizontal direction that is parallel to the sidewalls of the uniform width semiconductor region. For each tapered sidewall of the first and second tapered semiconductor regions, the taper angle can be the same throughout the tapered sidewall, or can vary as a function of a lateral distance from the uniform width semiconductor region. The uniform width semiconductor region, the first tapered semiconductor region, and the second tapered semiconductor region can have the same height, which can be the height of the top semiconductor layer 30L. In one embodiment, distal portions (i.e., the portions that are distal from the uniform width semiconductor region) of the first and second tapered semiconductor regions can have a curved surface, which can be, for example, vertical surfaces having a horizontal cross-section of an arc of a circle or an ellipse.

Referring to FIGS. 3A-3F, a selected portion of the exemplary structure including the uniform width semiconductor region of the template structure 30 is shown. Optionally, a pair of electrode plates (32A, 32B) can be formed on sidewalls of the template structure 30. The pair of electrode plates (32A, 32B) includes a first electrode plate 32A located on one sidewall of the uniform width semiconductor region of the template structure 30 and a second electrode plate 32B located on the other sidewall of the uniform width semiconductor region. The pair of electrode plates (32A, 32B) can be formed, for example, by depositing a conductive material by a non-conformal deposition method, and by patterning the deposited conductive material. The conductive material can be a metal, an intermetallic alloy, or a conductive metallic compound such as a conductive metallic nitride or conductive metallic carbide. In one embodiment, the conductive material can be Palladium. The non-conformal deposition method can be vacuum evaporation, molecular beam deposition, physical vapor deposition (sputtering), or any other deposition method known in the art that can deposit a material only on horizontal surface of the exemplary structure without deposition of any significant amount of material on vertical surfaces of the exemplary structure.

In one embodiment, the conductive material is deposited on the top surface of the first dielectric material layer 20 and the top surface of the template structure 30, and is subsequently patterned, for example, by applying a photoresist layer (not shown), lithographically patterning the photoresist layer, and etching physically exposed portions of the conductive material employing the patterned photoresist layer as an etch mask. The photoresist layer can be subsequently removed. Two remaining portions of the conductive material constitute the pair of electrode plates (32A, 32B). Alternately, a masking structure with an opening therein may be employed during the deposition of the conductive material. In this case, the pair of electrode plates (32A, 32B) is portions of the conductive material that passes through the opening and is deposited on the top surface of the first dielectric material layer 20, and remaining portions are lifted off during removal of the masking structure In one embodiment, a conductive material portion 32C contacting a top surface of the template structure 30 may be collaterally formed during formation of the pair of electrode plates (32A, 32B).

The thickness of the pair of electrode plates (32A, 32B) can be less than the height, i.e., the thickness, of the template structure 30. If any residual conductive material is deposited on sidewalls of the template structure 30 above the horizontal plane of the top surface of the pair of electrode plates (32A, 32B), an isotropic etch may be employed to remove such residual conductive material and to provide electrical isolation between the pair of electrode plates (32A, 32B) and the conductive material portion 32C.

Optionally, a thin, non-conductive barrier layer material (not shown) may be deposited at this point so that the entire template structure except for the portion in contact with the electrode plates (32A, 32B) is covered. In this case, the ratcheting electrodes formed in the later steps described below would be protected from the fluids flowing within the nanofluidics channel by a barrier layer. This barrier layer can be, for example, $HfO_2$ or $Al_2O_3$.

Figure 4D:
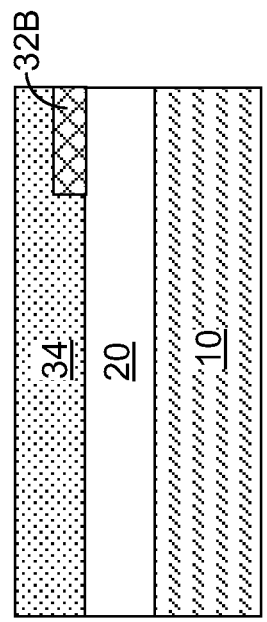
FIG. 4D is a vertical cross-sectional view of the selected portion of the exemplary structure along the vertical plane D-D' of FIG. 4A.
Figure 4E:
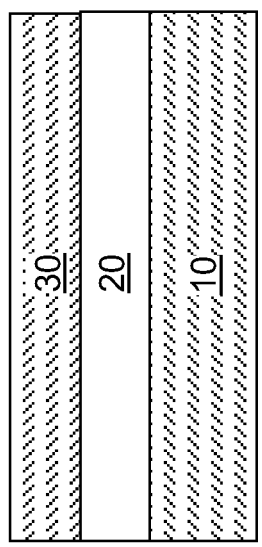
FIG. 4E is a vertical cross-sectional view of the selected portion of the exemplary structure along the vertical plane E-E' of FIG. 4A.
Figure 4F:
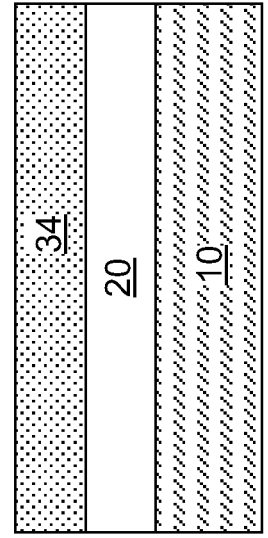
FIG. 4F is a vertical cross-sectional view of the selected portion of the exemplary structure along the vertical plane F-F' of FIG. 4A.
Figure 5B:
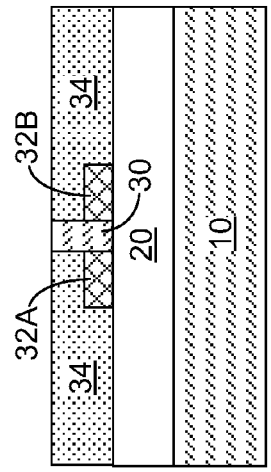
FIG. 5B is a vertical cross-sectional view of the selected portion of the exemplary structure along the vertical plane B-B' of FIG. 5A.
Figure 5C:
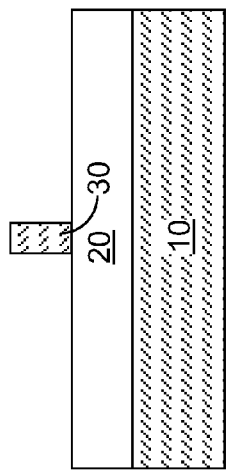
FIG. 5C is a vertical cross-sectional view of the selected portion of the exemplary structure along the vertical plane C-C' of FIG. 5A.
Figure 5A:
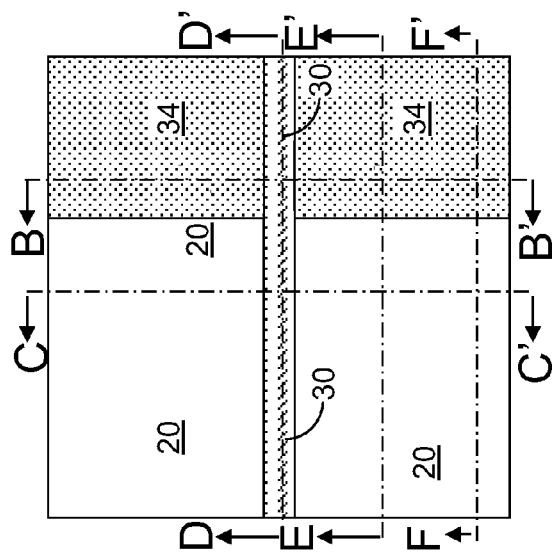
FIG. 5A is a top-down view of the selected portion of the exemplary structure after patterning of the dielectric masking material layer according to an embodiment of the present disclosure.
Figure 5D:
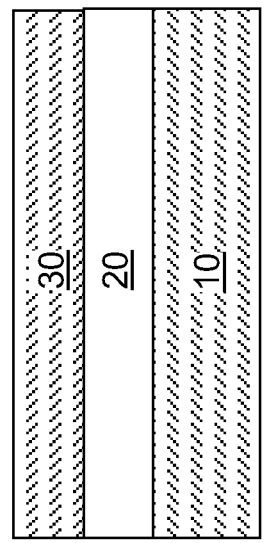
FIG. 5D is a vertical cross-sectional view of the selected portion of the exemplary structure along the vertical plane D-D' of FIG. 5A.
Figure 5E:
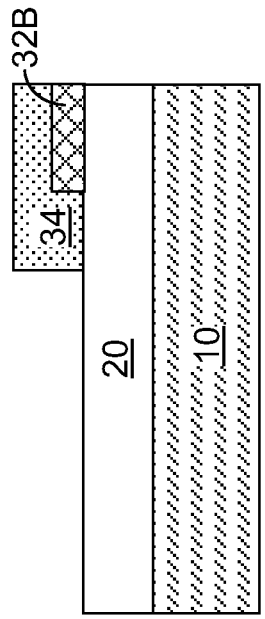
FIG. 5E is a vertical cross-sectional view of the selected portion of the exemplary structure along the vertical plane E-E' of FIG. 5A.
Figure 5F:
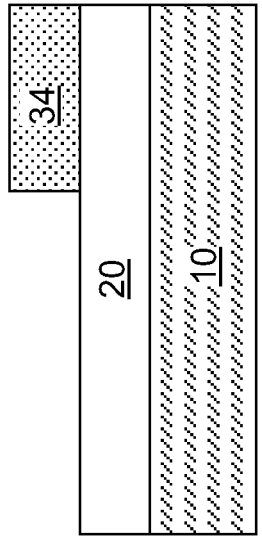
FIG. 5F is a vertical cross-sectional view of the selected portion of the exemplary structure along the vertical plane F-F' of FIG. 5A.
Figure 6B:
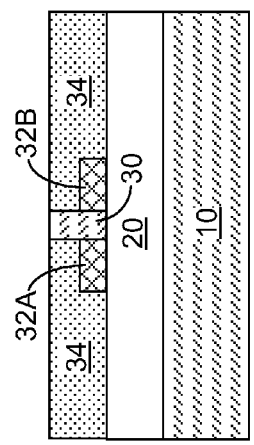
FIG. 6B is a vertical cross-sectional view of the selected portion of the exemplary structure along the vertical plane B-B' of FIG. 6A.
Figure 6C:
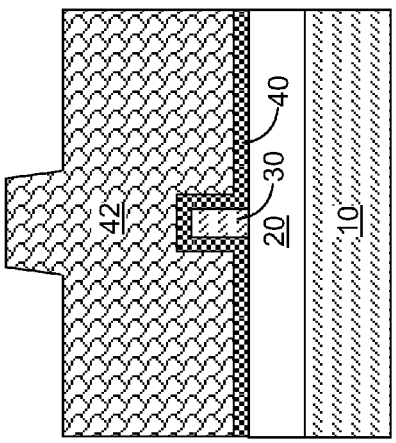
FIG. 6C is a vertical cross-sectional view of the selected portion of the exemplary structure along the vertical plane C-C' of FIG. 6A.
Figure 6A:
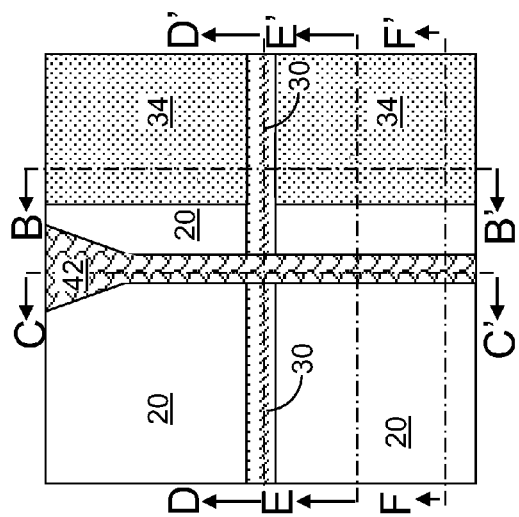
FIG. 6A is a top-down view of the selected portion of the exemplary structure after formation of an electrode line straddling the sacrificial template structure according to an embodiment of the present disclosure.
Figure 6D:
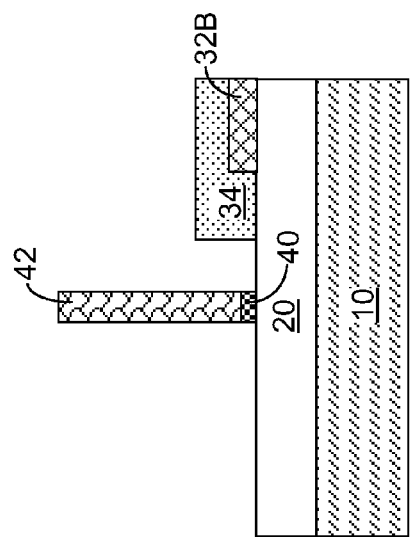
FIG. 6D is a vertical cross-sectional view of the selected portion of the exemplary structure along the vertical plane D-D' of FIG. 6A.
Figure 6E:
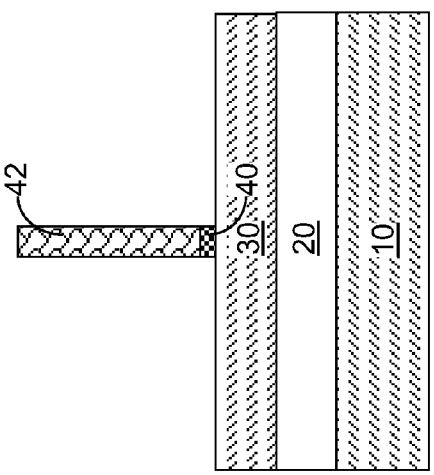
FIG. 6E is a vertical cross-sectional view of the selected portion of the exemplary structure along the vertical plane E-E' of FIG. 6A.
Figure 6F:
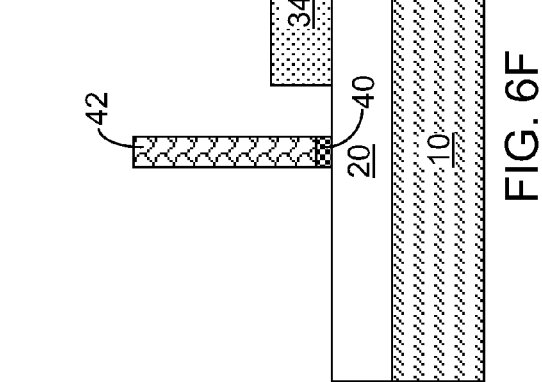
FIG. 6F is a vertical cross-sectional view of the selected portion of the exemplary structure along the vertical plane F-F' of FIG. 6A.
Figure 7D:
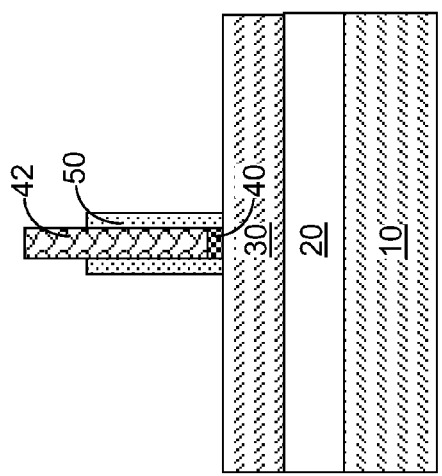
FIG. 7D is a vertical cross-sectional view of the selected portion of the exemplary structure along the vertical plane D-D' of FIG. 7A.
Figure 7E:
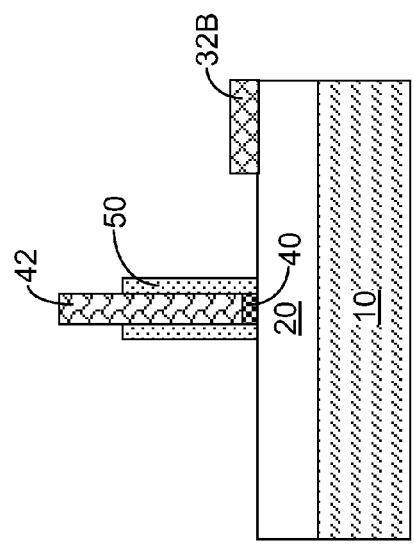
FIG. 7E is a vertical cross-sectional view of the selected portion of the exemplary structure along the vertical plane E-E' of FIG. 7A.
Figure 7F:
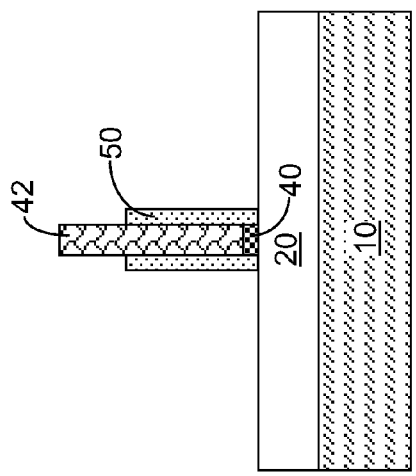
FIG. 7F is a vertical cross-sectional view of the selected portion of the exemplary structure along the vertical plane F-F' of FIG. 7A.
Figure 8B:
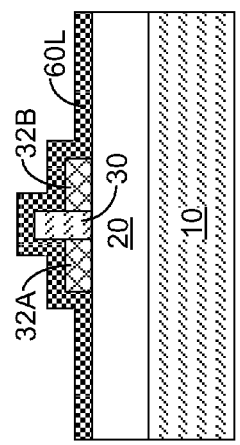
FIG. 8B is a vertical cross-sectional view of the selected portion of the exemplary structure along the vertical plane B-B' of FIG. 8A.
Figure 8C:
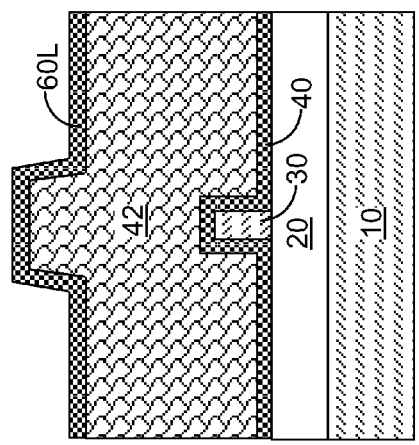
FIG. 8C is a vertical cross-sectional view of the selected portion of the exemplary structure along the vertical plane C-C' of FIG. 8A.
Figure 8A:
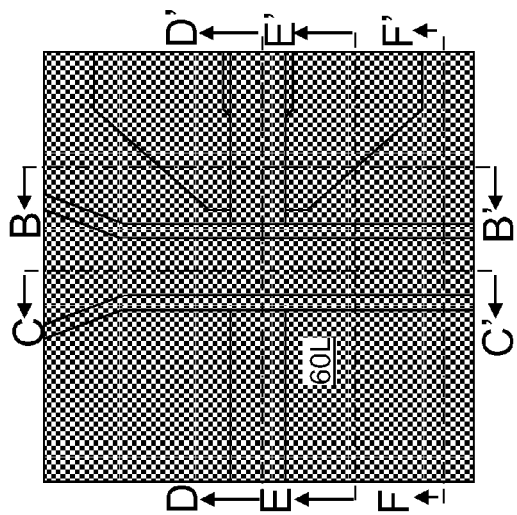
FIG. 8A is a top-down view of the selected portion of the exemplary structure after deposition of a conformal conductive layer on the dielectric spacer and the first dielectric material layer according to an embodiment of the present disclosure.
Figure 8D:
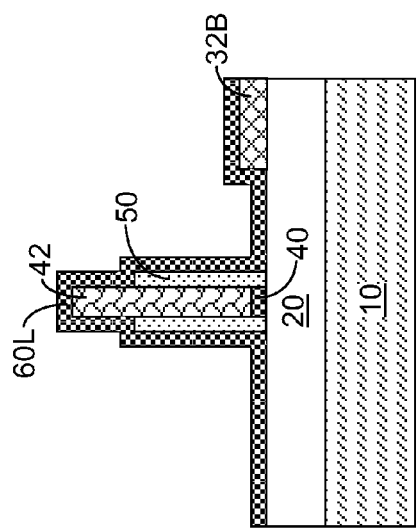
FIG. 8D is a vertical cross-sectional view of the selected portion of the exemplary structure along the vertical plane D-D' of FIG. 8A.
Figure 8E:
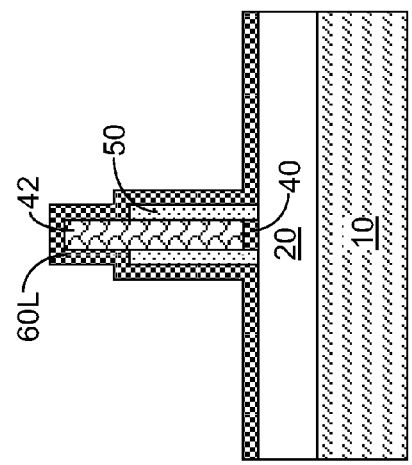
FIG. 8E is a vertical cross-sectional view of the selected portion of the exemplary structure along the vertical plane E-E' of FIG. 8A.
Figure 8F:
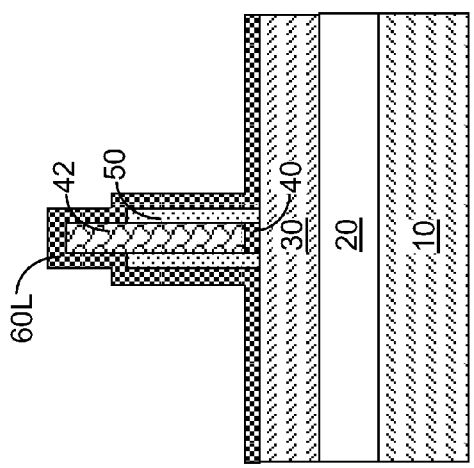
FIG. 8F is a vertical cross-sectional view of the selected portion of the exemplary structure along the vertical plane F-F' of FIG. 8A.
Figure 9D:
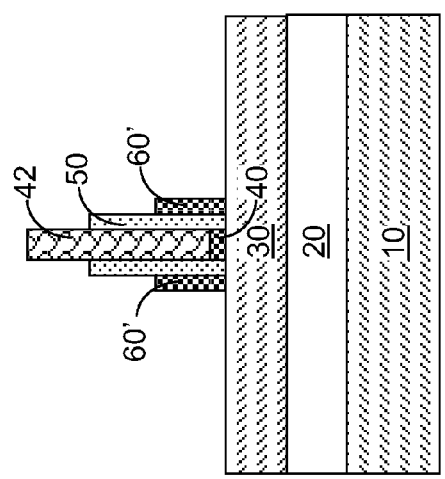
FIG. 9D is a vertical cross-sectional view of the selected portion of the exemplary structure along the vertical plane D-D' of FIG. 9A.
Figure 9E:
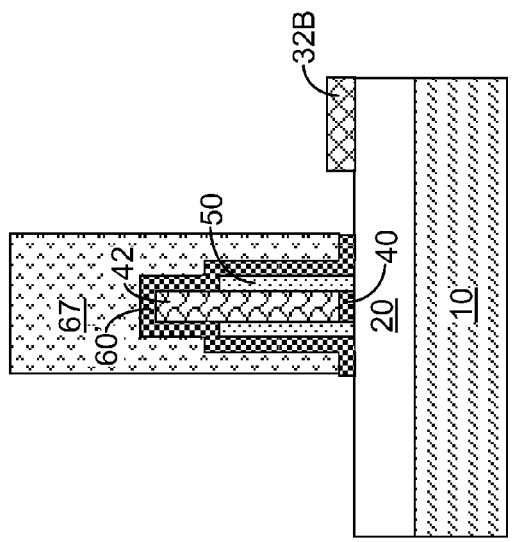
FIG. 9E is a vertical cross-sectional view of the selected portion of the exemplary structure along the vertical plane E-E' of FIG. 9A.
Figure 9F:
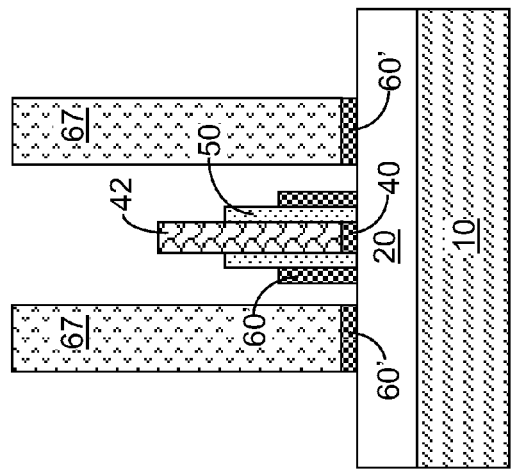
FIG. 9F is a vertical cross-sectional view of the selected portion of the exemplary structure along the vertical plane F-F' of FIG. 9A.
Figure 10B:
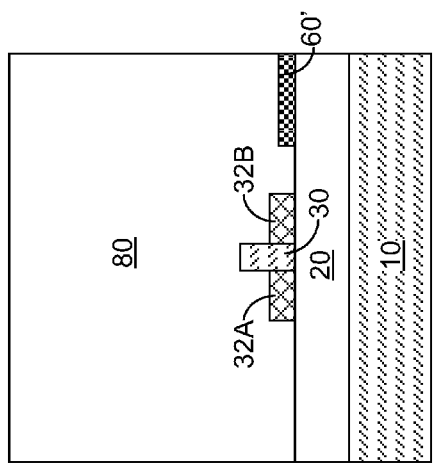
FIG. 10B is a vertical cross-sectional view of the selected portion of the exemplary structure along the vertical plane B-B' of FIG. 10A.
Figure 10C:
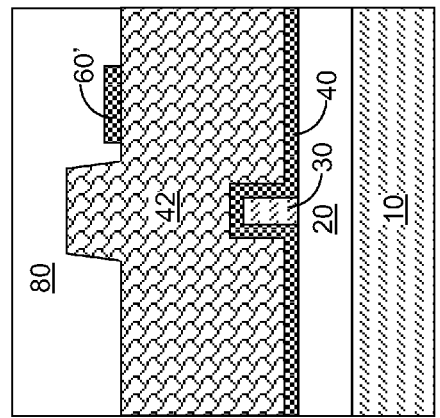
FIG. 10C is a vertical cross-sectional view of the selected portion of the exemplary structure along the vertical plane C-C' of FIG. 10A.
Figure 10A:
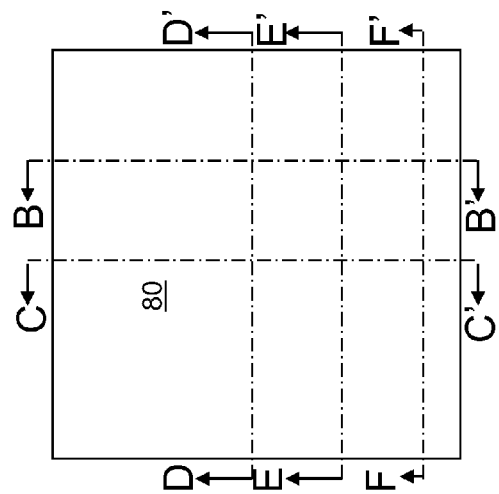
FIG. 10A is a top-down view of the selected portion of the exemplary structure after formation of a second dielectric material layer over the template structure according to an embodiment of the present disclosure.
Figure 10D:
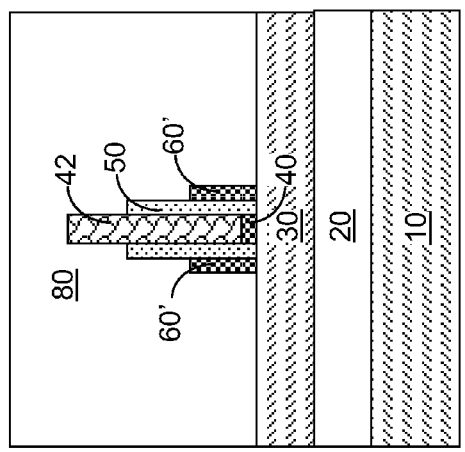
FIG. 10D is a vertical cross-sectional view of the selected portion of the exemplary structure along the vertical plane D-D' of FIG. 10A.
Figure 10E:
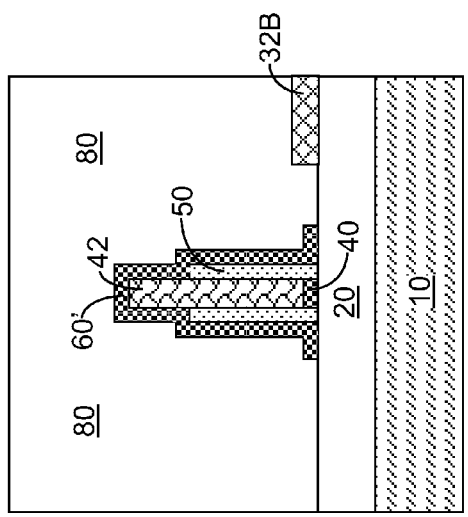
FIG. 10E is a vertical cross-sectional view of the selected portion of the exemplary structure along the vertical plane E-E' of FIG. 10A.
Figure 10F:
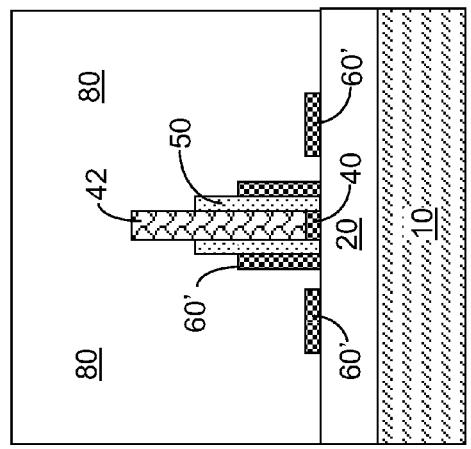
FIG. 10F is a vertical cross-sectional view of the selected portion of the exemplary structure along the vertical plane F-F' of FIG. 10A.
Figure 11B:
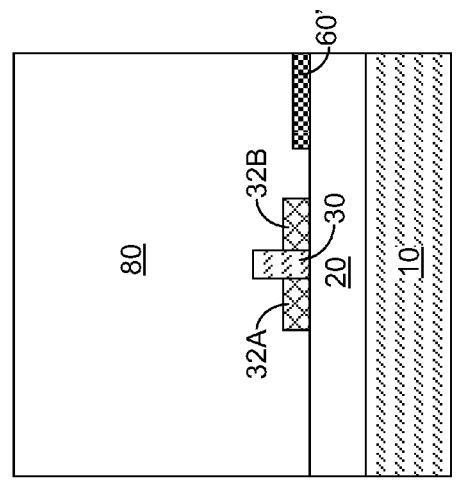
FIG. 11B is a vertical cross-sectional view of the selected portion of the exemplary structure along the vertical plane B-B' of FIG. 11A.
Figure 11C:
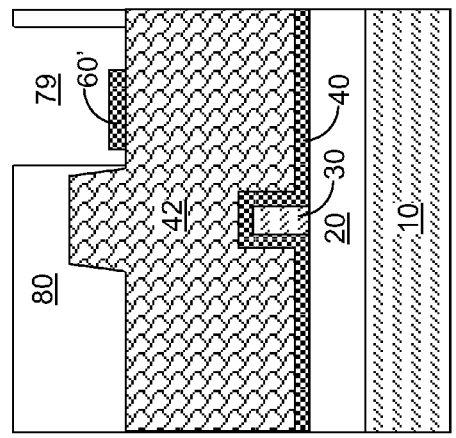
FIG. 11C is a vertical cross-sectional view of the selected portion of the exemplary structure along the vertical plane C-C' of FIG. 11A.
Figure 11A:
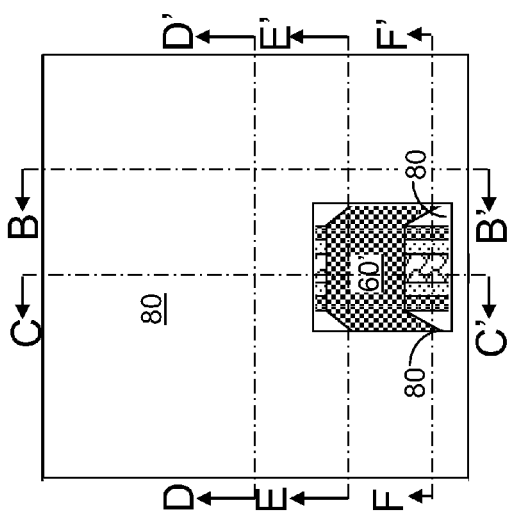
FIG. 11A is a top-down view of the selected portion of the exemplary structure after physically exposing a top surface of a remaining portion of the conformal conductive layer according to an embodiment of the present disclosure.
Figure 11D:
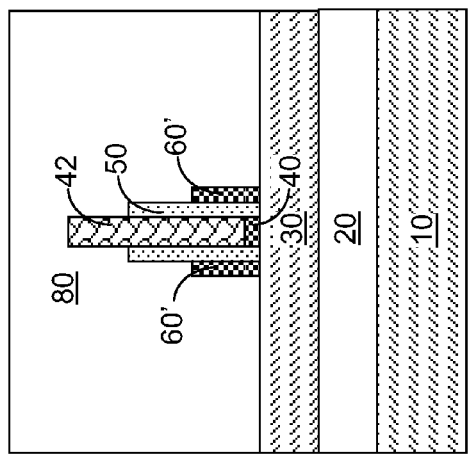
FIG. 11D is a vertical cross-sectional view of the selected portion of the exemplary structure along the vertical plane D-D' of FIG. 11A.
Figure 11E:
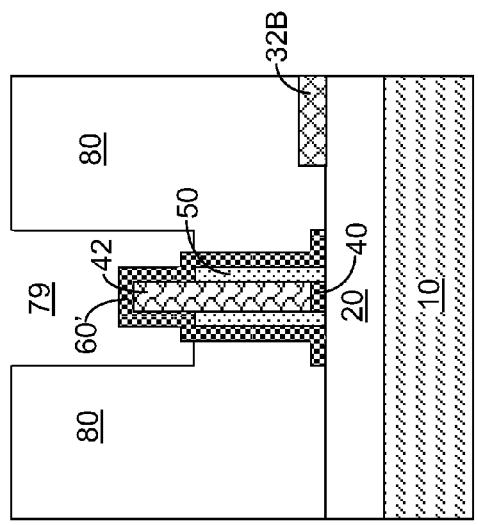
FIG. 11E is a vertical cross-sectional view of the selected portion of the exemplary structure along the vertical plane E-E' of FIG. 11A.
Figure 11F:
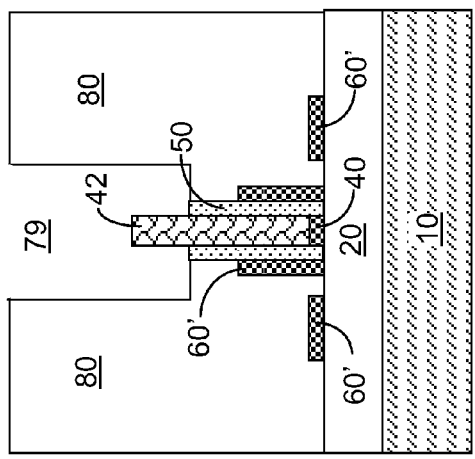
FIG. 11F is a vertical cross-sectional view of the selected portion of the exemplary structure along the vertical plane F-F' of FIG. 11A.
Figure 12B:
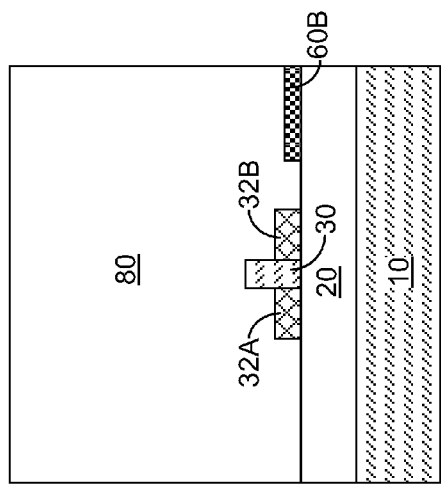
FIG. 12B is a vertical cross-sectional view of the selected portion of the exemplary structure along the vertical plane B-B' of FIG. 12A.
Figure 12C:
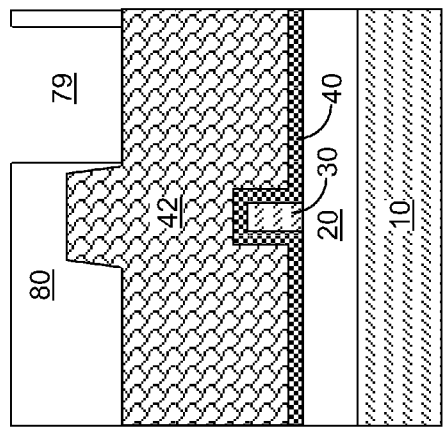
FIG. 12C is a vertical cross-sectional view of the selected portion of the exemplary structure along the vertical plane C-C' of FIG. 12A.
Figure 12A:
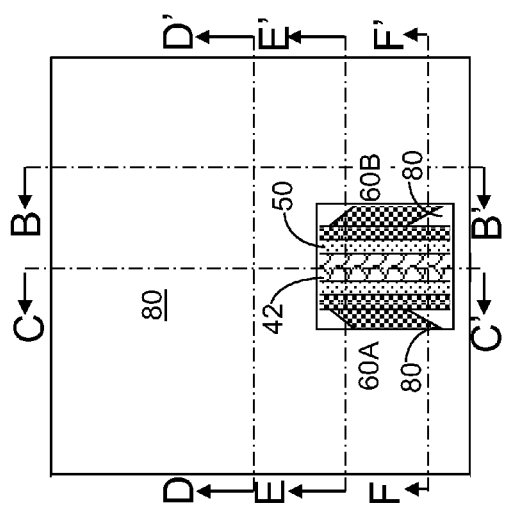
FIG. 12A is a top-down view of the selected portion of the exemplary structure after formation of a pair of peripheral electrodes according to an embodiment of the present disclosure.
Figure 12D:
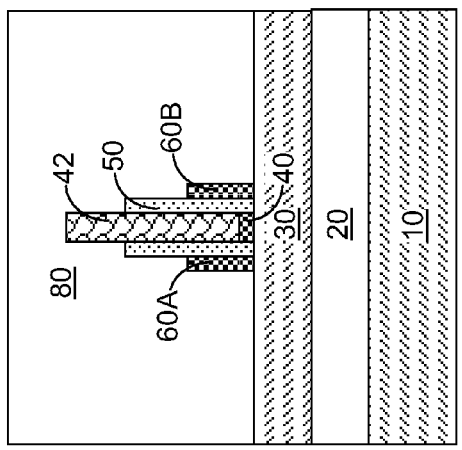
FIG. 12D is a vertical cross-sectional view of the selected portion of the exemplary structure along the vertical plane D-D' of FIG. 12A.
Figure 12E:
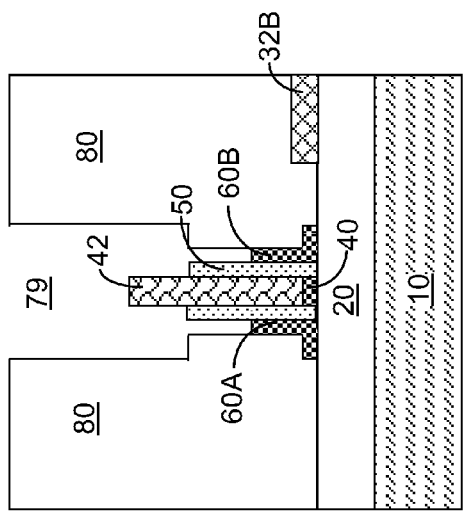
FIG. 12E is a vertical cross-sectional view of the selected portion of the exemplary structure along the vertical plane E-E' of FIG. 12A.
Figure 12F:
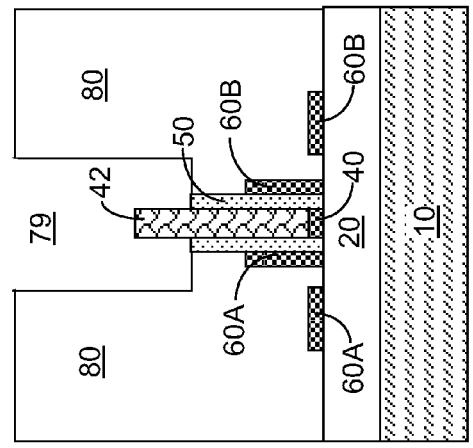
FIG. 12F is a vertical cross-sectional view of the selected portion of the exemplary structure along the vertical plane F-F' of FIG. 12A.

Referring to FIGS. 4A-4C, a dielectric masking material layer 34 is deposited and planarized. In one embodiment, the dielectric masking material layer 34 can be formed by applying a self-planarizing material such as a spin-on glass (SOG). The conductive material portion 32C can be removed, for example, by a wet etch or a dry etch that is selective to the dielectric masking material layer 34.

Alternately, the dielectric masking material layer 34 can be formed by deposition of a dielectric material and a subsequent planarization of the dielectric material. The dielectric material can include, for example, silicon oxide, silicon nitride, silicon oxynitride, porous or non-porous organosilicate glass, or combinations thereof. The conductive material portion 32C can be removed during a planarization process while employing the template structure 30 as a planarization stop structure. The planarization process can employ, for example, chemical mechanical planarization (CMP).

Referring to FIGS. 5A-5F, the dielectric masking material layer 34 can be patterned, for example, by applying a photoresist layer (not shown), patterning the photoresist layer so that a remaining portion of the photoresist layer after lithographic development covers the pair of electrode plates (32A, 32B), and removing physically exposed portions of the dielectric masking material layer 34, for example, by an etch. The removal of the physically exposed portions of the dielectric masking material layer 34 can be performed selective to the template structure 30. For example, if the dielectric masking material layer 34 includes silicon oxide, a wet etch employing hydrofluoric acid can be employed to remove physically exposed portions of the dielectric masking material layer 34. The photoresist layer can be subsequently removed, for example, by ashing.

Referring to FIGS. 6A-6F, an electrode line (40, 42) straddling the template structure 30 is formed. The electrode line (40, 42) includes at least one conductive material. The electrode line (40, 42) can be formed, for example, by depositing at least one conductive material layer, applying a photoresist layer over the at least one conductive material layer, lithographically patterning the photoresist layer, and transferring the pattern of the photoresist layer through the at least one conductive material employing an etch, which can be an anisotropic etch such as a reactive ion etch. An overetch may be used to clear the conductive material from the sidewalls of the template structure. Optionally, a lateral etch can be employed to reduce the lateral dimension of the electrode line (40, 42) during the pattern transfer from the photoresist layer into the at least one conductive material layer.

In one embodiment, the at least one conductive material layer can include a vertical stack of a metallic electrode material layer and a semiconductor electrode material layer. The metallic electrode material layer includes a metallic material such as an elemental metal, an alloy of at least two elemental metals, a conductive metallic compound including at least one elemental metal and at least one non-metallic element, or combinations thereof. For example, the metallic electrode material layer can include Ti, Ta, W, TiN, TaN, WN, TiC, TaC, WC, or combinations thereof. The semiconductor electrode material layer includes a doped elemental semiconductor material or a doped compound semiconductor material. Dopants in the semiconductor electrode material layer can be p-type dopants or n-type dopants. The vertical stack of the metallic electrode material layer and the semiconductor electrode material layer is subsequently patterned to form the electrode line (40, 42), which includes a metallic electrode line 40 and a semiconductor electrode line 42. The thickness of the electrode line (40, 42) can be from 15 nm to 1,000 nm, although lesser and greater thicknesses can also be employed.

In one embodiment, the thickness of the electrode line (40, 42) can be greater than the thickness of the template structure 30. The width of the electrode line (40, 42), as measured at a portion having a uniform width, can be from 3 nm to 20 nm, although lesser and greater width can also be employed. The width of the electrode line (40, 42) may increase in a region that does not overlie the template structure 30 to facilitate subsequent formation of a contact via structure thereupon.

Referring to FIGS. 7A-7F, a dielectric spacer 50 can be formed around the electrode line (40, 42). The dielectric spacer 50 can be formed, for example, by depositing a conformal dielectric material layer and anisotropically etching the conformal dielectric material layer. Horizontal portions of the conformal dielectric material layer are removed by the anisotropic etch, and a remaining vertical portion of the conformal dielectric material layer around the electrode line (40, 42) constitutes the dielectric spacer 50. The thickness of the dielectric spacer 50, as measured laterally on sidewalls of the electrode line (40, 42), can be from 1 nm to 20 nm, although lesser and greater thicknesses can also be employed. If the thickness of the electrode line (40, 42) is greater than the thickness of the template structure 30, the conformal dielectric material layer can be removed from sidewalls of the template structure 30 by an anisotropic overetch. If the dielectric spacer 50 is composed of the same material as the dielectric masking material layer 34, or if they are etched in similar chemistries, the dielectric masking material layer 34 may be removed during the overetch of the dielectric spacer material 50.

Referring to FIGS. 8A-8F, a conformal conductive layer 60L is deposited on the dielectric spacer 50 and the first dielectric material layer 20. The conformal conductive material layer 60L includes a conductive material, which can be, for example, a metallic material and/or a doped semiconductor material. The metallic material can be an elemental metal, an alloy of at least two elemental metals, a conductive metallic compound including at least one elemental metal and at least one non-metallic element, or combinations thereof. For example, the metallic material can include Ti, Ta, W, TiN, TaN, WN, TiC, TaC, WC, or combinations thereof. The doped semiconductor material can be a doped elemental semiconductor material or a doped compound semiconductor material. In one embodiment, the conformal conductive material layer 60 can be a metallic material layer.

The conformal conductive layer 60L is deposited directly on a top surface of the electrode line (40, 42), outer sidewall surfaces of the dielectric spacer 50, and the top surface of the first dielectric material layer 20. The thickness of the conformal conductive material layer 60L can be from 2 nm to 20 nm, although lesser and greater thicknesses can also be employed.

Referring to FIGS. 9A-9F, a photoresist layer 67 is applied and lithographically patterned such that a remaining portion of the photoresist layer 67 straddles the electrode line (40, 42) and cover horizontal portions of the conformal conductive layer 60L contacting the first dielectric material layer 20. Specifically, the photoresist layer 67 can be patterned such that a remaining portion of the photoresist layer 67 straddles portions of the electrode line (40, 42), the dielectric spacer 50, and the conformal conductive layer 60L that do not overlie the template structure 30 or the pair of electrode plates (32A, 32B).

An anisotropic etch is performed on the conformal conductive layer 60L employing the patterned photoresist layer 67 as an etch mask. Horizontal portions of the conformal conductive layer 60L are removed in regions in which the patterned photoresist layer 67 is not present. The material is overetched so that any portions of the conformal conductive layer 60L which are on the sidewalls of the template structure 30 or the electrode structures 32B are removed, but the overetch is limited such that portions of the conformal conductive layer 60L which are on the sidewalls of the electrode line (40,42) remain. Remaining portions of the conformal conductive layer 60L after the anisotropic etch constitutes a contiguous conductive material portion 60'. The contiguous conductive material portion 60' is a single contiguous structure, and includes portions of the conformal conductive layer 60L that are located underneath the photoresist layer 67. Further, the contiguous conductive material portion 60' includes vertical portions of the conformal conductive layer 60L that are not covered by the lithographically patterned photoresist layer 67. The patterned photoresist layer 67 can be subsequently removed, for example, by ashing.

Referring to FIGS. 10A-10F, a second dielectric material layer 80 is deposited over the template structure 30, the electrode line (40, 42), the dielectric spacer 50, the contiguous conductive material portion 60', and the pair of electrode plates (32A, 32B). The second dielectric material layer 80L includes a dielectric material such as silicon oxide, silicon nitride, silicon oxynitride, a dielectric metal oxide, a dielectric metal nitride, a dielectric metal oxynitride, or a combination thereof. The dielectric material of the second dielectric material layer 80 can be the same as, or can be different from the dielectric material of the first dielectric material layer 20. In one embodiment, the second dielectric material layer 80 can include a self-planarizing material such as spin-on glass (SOG). In another embodiment, the second dielectric material layer 80 can be planarized, for example, by chemical mechanical planarization.

Referring to FIGS. 11A-11F, a top surface of the contiguous conductive material portion 60', i.e., the remaining portion of the conformal conductive layer 60L, is physically exposed by forming a cavity 79 overlying a topmost subportion of the contiguous conductive material portion 60' that overlie the conductive line (40, 42). The cavity 79 can be formed, for example, by applying a photoresist layer (not shown) over the second dielectric material layer 80, patterning the photoresist layer to include a hole overlying the topmost subportion of the contiguous conductive material portion 60', and etching the portion of the second dielectric material layer 80 in the area of the hole within the patterned photoresist layer by an etch. The etch can be an anisotropic etch or an isotropic etch. The patterned photoresist layer is subsequently removed, for example, by ashing.

Referring to FIGS. 12A-12F, a pair of peripheral electrodes (60A, 60B) can be formed by patterning the remaining portion of the conformal conductive layer 60L, i.e., the contiguous conductive material portion 60'. Specifically, the physically exposed subportion of the contiguous conductive material portion 60' is removed from above the top surface of the electrode line (40, 42) within the cavity 79. Two remaining portions of the contiguous conductive material portion 60' that are disjoined by the removal of the physically exposed subportion of the contiguous conductive material portion 60' constitute the pair of peripheral electrodes (60A, 60B). The pair of peripheral electrodes (60A, 60B) include a first peripheral electrode 60A located on one side of the electrode line (40, 42) and a second peripheral electrode 60B located on the opposite side of the electrode line (40, 42). Each peripheral electrode (60A, 60B) includes a vertical portion that contact the dielectric spacer 50 and a horizontal portion that contacts the top surface of the first dielectric material layer 20. Each peripheral electrode (60A, 60B) is laterally spaced from the electrode line by the dielectric spacer 50. Each peripheral electrode (60A or 60B) is laterally spaced from the other peripheral electrode (60B or 60A) by the electrode line (40, 42) and the dielectric spacer 50.

Referring to FIGS. 13A-13F, the cavity 79 is filled with a dielectric material to form a dielectric fill material portion 81. The dielectric fill material portion 81 includes a dielectric material such as silicon oxide, silicon nitride, silicon oxynitride, porous or non-porous organosilicate glass (OSG), dielectric metal oxide, dielectric metal nitride, dielectric metal oxynitride, or a combination thereof. The dielectric fill material portion 81 can be formed by spin coating or by chemical vapor deposition followed by planarization. The dielectric fill material portion 81 is in contact with a top surface of the electrode line (40, 42), outer sidewalls of the dielectric spacer 50, and top surfaces and sidewall surface of the vertical portions of the peripheral electrodes (60A, 60B). Further, sidewalls of the dielectric fill material portion 81 can be in contact with the second dielectric material layer 80, and can be substantially vertical.

Various contact via structures (82, 84, 86, 88A, 88B) can be formed through the second dielectric material layer 80. The various contact via structures (82, 84, 86, 88A, 88B) can be formed, for example, by forming contact via cavities through the second dielectric material layer 80 and depositing a conductive material to fill the contact via cavities. Portions of the conductive material above the top surface of the second dielectric material layer 80 can be patterned to provide electrical isolation among the various contact via structures (82, 84, 86, 88A, 88B). The contact via structures (82, 84, 86, 88A, 88B) can include an electrode line contact via structure 82 that contacts the electrode line (40, 42), a first peripheral electrode contact via structure 84 that contacts the first peripheral electrode 60A, a second peripheral electrode contact via structure 86 that contacts the second peripheral electrode line 60B, a first electrode plate contact via structure 88A that contacts the first electrode plate 32A, and a second electrode plate contact via structure 88B that contacts the second electrode plate 32B.

Referring to FIGS. 14A and 14B, a first via cavity 91 and a second via cavity 93 are formed through the second dielectric material layer 80. The first via cavity 91 overlies a distal end of the first tapered semiconductor region of the template structure 30, and the second via cavity 93 overlies a distal end of the second tapered semiconductor region of the template structure 30. The first and second via cavities (91, 93) can be formed, for example, by applying a photoresist layer (nor shown) above the second dielectric material layer 80, lithographically patterning the photoresist layer to form two holes overlying the distal end of the first tapered semiconductor region and the distal end of the second tapered semiconductor region, respectively, and transferring the pattern of the photoresist layer through the second dielectric material layer 80 by an etch. The etch can be an anisotropic etch or an isotropic etch. The lateral dimension of each of the first and second via cavities (91, 93) can be from 100 nm to 10 microns, although lesser and greater lateral dimensions can also be employed. In one embodiment, a horizontal cross-sectional shape of each of the first and second via cavities (91, 93) can be circular or elliptical, and the lateral dimension of each of the first and second via cavities (91, 93) can be a diameter of a circle or a semimajor axis of an ellipse.

Figure 15A:
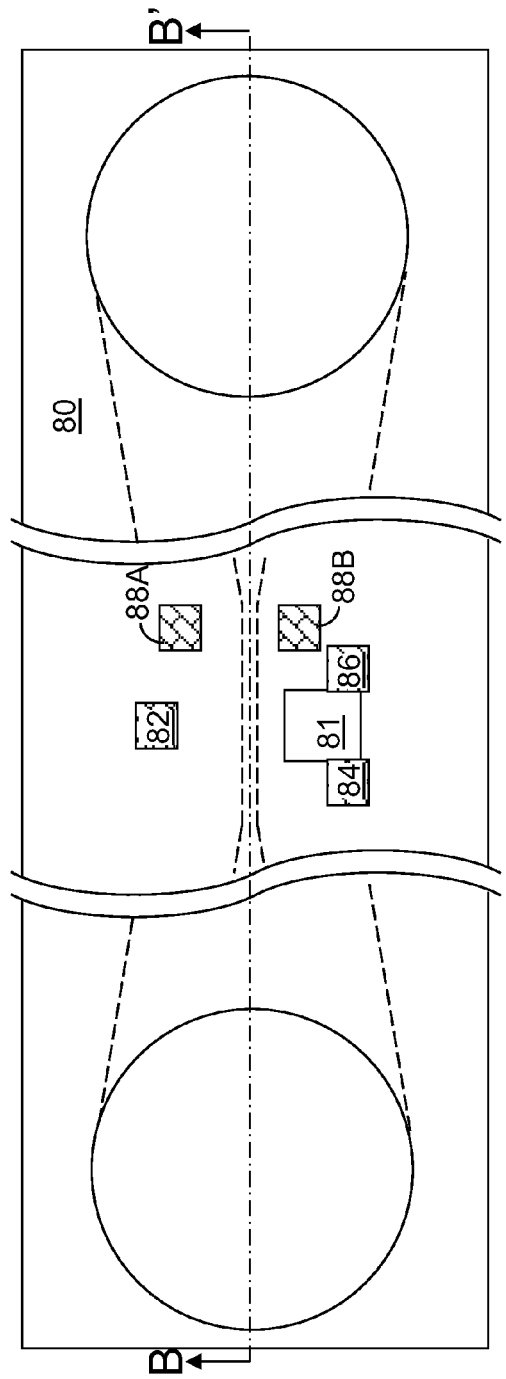
FIG. 15A is a top-down view of the exemplary structure after removal of the template structure to form a cavity according to an embodiment of the present disclosure.
Figure 15B:
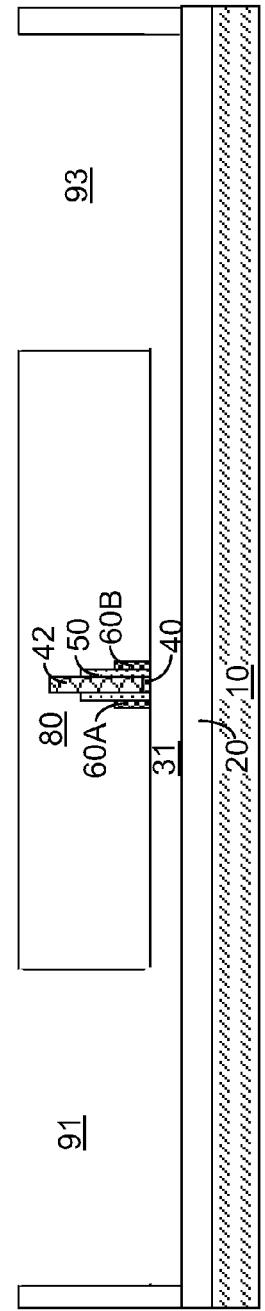
FIG. 15B is a vertical cross-sectional view of the exemplary structure along the vertical plane B-B' of FIG. 15A.

Referring to FIGS. 15A and 15B, the template structure 30 is removed to form a cavity 31 that extends along the lateral (horizontal) direction. The cavity 31 connects the first via cavity 91 and a second via cavity 93 so that a nanoscale string such as a DNA strand can sequentially pass through the first via cavity 91, the cavity 31, and the second via cavity 93. The contiguous cavity (91, 31, 93) can be employed as a part of a sensor structure in conjunction with any of the various electrode structures, which include the electrode line (40, 42), the pair of peripheral electrodes (60A, 60B), and the pair of electrode plates (32A, 32B).

The sensor structure includes a first dielectric material layer 20 and a second dielectric material layer 80 in contact with each other at a planar interface. A cavity 31 is embedded within the first dielectric material layer 20 and the second dielectric material layer 80. The sensor structure further includes an electrode line (40, 42) embedded within the second dielectric material layer 80 and straddling the cavity 31. First portions of the electrode line (40, 42) are in contact with a surface of the first dielectric material layer 20, and a second portion of the electrode line (40, 42) that is not in contact with the first dielectric material layer 20 is spaced from a plane including the interface by a uniform distance which is equal to the thickness (height) of the template structure 30.

The sensor structure can further include a dielectric spacer 50 laterally surrounding the electrode line (40, 42). First portions of the dielectric spacer 50 are in contact with the first dielectric material layer 20, and a second portion of the dielectric spacer 50 that is not in contact with the first dielectric material layer 20 and overlying the cavity 31 is spaced from the plane including the interface by the uniform distance, which is equal to the thickness (height) of the template structure 30.

The peripheral electrodes (60A, 60B) are laterally spaced from the electrode line (40, 42) by the dielectric spacer 50. Each of the peripheral electrodes includes first portions that are in contact with first dielectric material layer 20, and a second portion that is not in contact with the first dielectric material layer 20 and is spaced from the plane including the interface by the uniform distance, which is equal to the thickness (height) of the template structure 30. The peripheral electrodes (60A, 60B) are in contact with outer sidewalls of the dielectric spacer 50. The topmost portion of the dielectric spacer 50 can protrude above the topmost portions of the peripheral electrodes (60A, 60B). In this case, a portion of the dielectric spacer 50 is spaced farther away from the first dielectric material layer 20 than any portion of the peripheral electrodes (60A, 60B). A portion of each of the peripheral electrodes (60A, 60B) can have an L-shaped vertical cross-sectional shape.

In one embodiment, the electrode line (40, 42) can have the same height except for region overlying edges of the cavity 31. In this case, a vertical distance between a bottom surface and a top surface of the electrode line (40, 42) can be invariant under lateral translation. Further, a vertical distance between a top surface and a bottom surface of the first portions of the electrode line that contact the first dielectric material layer 20 can be the same as a vertical distance between a top surface and a bottom surface of the second portion of the electrode line overlying the cavity 31.

The cavity 31 includes a uniform width cavity portion having a uniform width throughout and corresponding to the volume from which the uniform width semiconductor region is removed, a first tapered cavity portion adjoined to the uniform width cavity portion at a proximal end thereof and having a first variable width that increases with distance from the uniform width cavity portion and corresponding to the volume from which the first tapered semiconductor region is removed, and a second tapered cavity portion adjoined to the uniform width cavity portion at a proximal end thereof and having a second variable width that increases with distance from the uniform width cavity portion and corresponding to the volume from which the second tapered semiconductor region is removed. The uniform width cavity portion, the first tapered cavity portion, and the second tapered cavity portion can have a same height, which is the height of the template structure 30.

The sensor structure further includes a first via cavity 91 extending through the second dielectric material layer 80 and located over a distal end of the first tapered cavity portion, and a second via cavity 93 extending through the second dielectric material layer 80 and located over a distal end of the second tapered cavity portion. The first via cavity 91 and the second via cavity 93 can include substantially vertical sidewalls adjoining the first tapered cavity portion or the second tapered cavity portion, respectively.

The pair of electrode plates (32A, 32B), if formed, are located on sidewalls of cavity 31. The pair of electrode plates (32A, 32B) can have the same thickness throughout. The same thickness can be less than the vertical height of the cavity 31.

The various electrodes (40, 42, 60A, 60B, 32A, 32B) can be employed to apply an electrical bias voltage, to flow an electrical current, or to measure a local resistance of any nanoscale string such as a DNA strand that passes through the cavity 31. Further, the wider opening at the distal ends of the cavity 31 and the first and second via cavities (91, 93) enable manipulation of the nanoscale string to guide the nanoscale string through the cavity 31. The sensor structure of the present disclosure can provide useful electrical measurements on nanoscale strings.

While the disclosure has been described in terms of specific embodiments, it is evident in view of the foregoing description that numerous alternatives, modifications and variations will be apparent to those skilled in the art. Each of the embodiments described herein can be implemented individually or in combination with any other embodiment unless expressly stated otherwise or clearly incompatible. Accordingly, the disclosure is intended to encompass all such alternatives, modifications and variations which fall within the scope and spirit of the disclosure and the following claims.

What is claimed is:

1. A sensor structure comprising:
a first dielectric material layer and a second dielectric material layer in contact with each other at a planar interface, wherein a cavity is embedded within said second dielectric material layer and located above said first dielectric material layer;
an electrode line embedded within said second dielectric material layer and straddling said cavity, wherein first portions of said electrode line are in contact with a surface of said first dielectric material layer, and a second portion of said electrode line that is not in contact with said first dielectric material layer is spaced from a plane including said interface by a uniform distance; and
a dielectric spacer laterally surrounding said electrode line, wherein first portions of said dielectric spacer are in contact with said first dielectric material layer, and a second portion of said dielectric spacer that is not in contact with said first dielectric material layer is spaced from said plane including said interface by said uniform distance.

2. The sensor structure of claim 1, further comprising peripheral electrodes laterally spaced from said electrode line by said dielectric spacer.

3. The sensor structure of claim 2, wherein each of said peripheral electrodes includes:
first portions that are in contact with first dielectric material layer; and
a second portion that is not in contact with said first dielectric material layer, and is spaced from said plane including said interface by said uniform distance.

4. The sensor structure of claim 2, wherein said peripheral electrodes are in contact with outer sidewalls of said dielectric spacer.

5. The sensor structure of claim 2, wherein a portion of said dielectric spacer is spaced farther away from said first dielectric material layer than any portion of said peripheral electrodes.

6. The sensor structure of claim 2, wherein a portion of each of said peripheral electrodes has an L-shaped vertical cross-sectional shape.

7. The sensor structure of claim 2, further comprising a dielectric fill material portion in contact with a top surface of said electrode line, outer sidewalls of said dielectric spacer, and top surfaces of peripheral electrodes.

8. The sensor structure of claim 7, wherein sidewalls of said dielectric fill material portion are in contact with said second dielectric material layer, and are substantially vertical.

9. A sensor structure comprising:
a first dielectric material layer and a second dielectric material layer in contact with each other at a planar interface, wherein a cavity is embedded within said second dielectric material layer and located above said first dielectric material layer; and
an electrode line embedded within said second dielectric material layer and straddling said cavity, wherein first portions of said electrode line are in contact with a surface of said first dielectric material layer, and a second portion of said electrode line that is not in contact with said first dielectric material layer is spaced from a plane including said interface by a uniform distance,
wherein a vertical distance a top surface and a bottom surface of a first portion of said electrode line in contact with said first dielectric material layer is the same as a vertical distance between a top surface and a bottom surface of a second portion of said electrode line overlying said cavity.

10. The sensor structure of claim 9, further comprising a dielectric spacer laterally surrounding said electrode line, wherein first portions of said dielectric spacer are in contact with said first dielectric material layer, and a second portion of said dielectric spacer that is not in contact with said first dielectric material layer is spaced from said plane including said interface by said uniform distance.

11. The sensor structure of claim 10, further comprising peripheral electrodes laterally spaced from said electrode line by said dielectric spacer, and wherein each of said peripheral electrodes includes:
first portions that are in contact with first dielectric material layer; and
a second portion that is not in contact with said first dielectric material layer, and is spaced from said plane including said interface by said uniform distance.

12. The sensor structure of claim 11, wherein said peripheral electrodes are in contact with outer sidewalls of said dielectric spacer, and wherein a portion of said dielectric spacer is spaced farther away from said first dielectric material layer than any portion of said peripheral electrodes.

13. The sensor structure of claim 11, further comprising a dielectric fill material portion in contact with a top surface of said electrode line, outer sidewalls of said dielectric spacer, and top surfaces of peripheral electrodes, wherein sidewalls of said dielectric fill material portion are in contact with said second dielectric material layer, and are substantially vertical.

14. The sensor structure of claim 9, wherein said cavity comprises:

a uniform width cavity portion having a uniform width throughout;

a first tapered cavity portion adjoined to said uniform width cavity portion at a proximal end thereof and having a first variable width that increases with distance from said uniform width cavity portion; and a second tapered cavity portion adjoined to said uniform width cavity portion at a proximal end thereof and having a second variable width that increases with distance from said uniform width cavity portion.

15. A sensor structure comprising:

a first dielectric material layer and a second dielectric material layer in contact with each other at a planar interface, wherein a cavity is embedded within said second dielectric material layer and located above said first dielectric material layer; and an electrode line embedded within said second dielectric material layer and straddling said cavity, wherein first portions of said electrode line are in contact with a surface of said first dielectric material layer, and a second portion of said electrode line that is not in contact with said first dielectric material layer is spaced from a plane including said interface by a uniform distance, wherein said cavity comprises:

a uniform width cavity portion having a uniform width throughout;

a first tapered cavity portion adjoined to said uniform width cavity portion at a proximal end thereof and having a first variable width that increases with distance from said uniform width cavity portion; and a second tapered cavity portion adjoined to said uniform width cavity portion at a proximal end thereof and having a second variable width that increases with distance from said uniform width cavity portion.

16. The sensor structure of claim 15, wherein said uniform width cavity portion, said first tapered cavity portion, and said second tapered cavity portion have a same height.

17. The sensor structure of claim 15, further comprising a dielectric spacer laterally surrounding said electrode line, wherein first portions of said dielectric spacer are in contact with said first dielectric material layer, and a second portion of said dielectric spacer that is not in contact with said first dielectric material layer is spaced from said plane including said interface by said uniform distance.

18. The sensor structure of claim 17, further comprising peripheral electrodes laterally spaced from said electrode line by said dielectric spacer, wherein each of said peripheral electrodes includes:

first portions that are in contact with first dielectric material layer; and a second portion that is not in contact with said first dielectric material layer, and is spaced from said plane including said interface by said uniform distance.

19. The sensor structure of claim 18, wherein said peripheral electrodes are in contact with outer sidewalls of said dielectric spacer, and wherein a portion of said dielectric spacer is spaced farther away from said first dielectric material layer than any portion of said peripheral electrodes.

20. The sensor structure of claim 18, further comprising a dielectric fill material portion in contact with a top surface of said electrode line, outer sidewalls of said dielectric spacer, and top surfaces of peripheral electrodes, wherein sidewalls of said dielectric fill material portion are in contact with said second dielectric material layer, and are substantially vertical.

* * * * *